United States Patent
Edwards et al.

(10) Patent No.: US 11,752,323 B2
(45) Date of Patent: Sep. 12, 2023

(54) ELECTROMAGNETICALLY DRIVEN BLOOD PUMP

(71) Applicant: Boston Scientific Scimed Inc, Maple Grove, MN (US)

(72) Inventors: Nathan Edwards, Minneapolis, MN (US); Benjamin Breidall, Eden Prairie, MN (US); Joseph A. Kronstedt, New Hope, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 129 days.

(21) Appl. No.: 17/137,185

(22) Filed: Dec. 29, 2020

(65) Prior Publication Data

US 2021/0220637 A1    Jul. 22, 2021

Related U.S. Application Data

(60) Provisional application No. 62/964,102, filed on Jan. 21, 2020.

(51) Int. Cl.
| | |
|---|---|
| *A61M 60/818* | (2021.01) |
| *A61M 60/419* | (2021.01) |
| *A61M 60/216* | (2021.01) |
| *F04D 13/06* | (2006.01) |

(52) U.S. Cl.
CPC ........ *A61M 60/419* (2021.01); *A61M 60/216* (2021.01); *A61M 60/818* (2021.01); *F04D 13/06* (2013.01); *F04D 13/064* (2013.01); *F04D 13/0633* (2013.01); *A61M 2207/00* (2013.01)

(58) Field of Classification Search
CPC ............ A61M 60/419; A61M 2207/00; A61M 60/13; A61M 60/216; A61M 60/422; A61M 60/818; A61M 60/825; A61M 60/88; F04D 13/06; F04D 13/0633; F04D 13/064; F16C 11/0623; F16C 2316/18; F16C 3/02

See application file for complete search history.

(56) References Cited

U.S. PATENT DOCUMENTS

| | | | |
|---|---|---|---|
| 4,994,078 A | 2/1991 | Jarvik | |
| 5,376,114 A | 12/1994 | Jarvik | |
| 5,507,629 A * | 4/1996 | Jarvik | ............... F16C 39/063 417/423.12 |

(Continued)

FOREIGN PATENT DOCUMENTS

WO    2007140481 A2    12/2007

OTHER PUBLICATIONS

International Search Report and Written Opinion for International patent application No. PCT/US2020/067376, filed Dec. 29, 2020, dated Mar. 16, 2021.

(Continued)

*Primary Examiner* — Michael Lebentritt
(74) *Attorney, Agent, or Firm* — Faegre Drinker Biddle & Reath LLP

(57) ABSTRACT

Various aspects of the present disclosure are directed toward apparatuses, systems, and methods that may include a magnetic drive system of a blood pump. The magnetic drive system may include a drive shaft coupled to an impeller, a driven magnet assembly coupled to at least one of the drive shaft and the impeller, and a driving coil assembly configured to drive the driven magnet assembly.

18 Claims, 4 Drawing Sheets

(56) References Cited

U.S. PATENT DOCUMENTS

| | | | | |
|---|---|---|---|---|
| 5,588,812 | A * | 12/1996 | Taylor | F04D 13/0646 |
| | | | | 604/151 |
| 5,746,575 | A * | 5/1998 | Westphal | A61M 60/812 |
| | | | | 415/206 |
| 6,176,848 | B1 * | 1/2001 | Rau | F04D 29/047 |
| | | | | 600/16 |
| 7,011,620 | B1 | 3/2006 | Siess | |
| 8,734,508 | B2 * | 5/2014 | Hastings | A61M 60/50 |
| | | | | 623/3.1 |
| 10,172,985 | B2 * | 1/2019 | Simon | A61M 60/829 |
| 10,842,921 | B2 * | 11/2020 | Siess | A61M 60/824 |
| 2008/0269880 | A1 | 10/2008 | Jarvik | |
| 2015/0285258 | A1 * | 10/2015 | Foster | F04D 17/10 |
| | | | | 415/203 |
| 2018/0050142 | A1 * | 2/2018 | Siess | A61M 60/825 |
| 2021/0199127 | A1 * | 7/2021 | Richert | F04D 29/0476 |
| 2021/0220636 | A1 * | 7/2021 | Schauer | A61M 60/216 |

OTHER PUBLICATIONS

International Preliminary Report on Patentability for International patent application No. PCT/US2020/067376, filed Dec. 29, 2020, dated Aug. 4, 2022.

\* cited by examiner

ELECTROMAGNETICALLY DRIVEN BLOOD PUMP

CROSS REFERENCE TO RELATED APPLICATION

This application claims priority to Provisional Application No. 62/964,102, filed Jan. 21, 2020, which is herein incorporated by reference in its entirety.

TECHNICAL FIELD

The present disclosure relates to percutaneous circulatory support devices. More specifically, the disclosure relates to motors and bearings using in percutaneous circulatory support devices.

BACKGROUND

Percutaneous circulatory support devices such as blood pumps typically are easier to implant and provide greater benefit if they are made to be as small as possible, without sacrificing functionality. Typically, a motor housed in a motor housing drives an impeller that is housed in a separate impeller housing.

SUMMARY

In Example 1, a magnetic drive system of a blood pump, the magnetic drive system includes a drive shaft coupled to an impeller and configured to rotate with the impeller; a driven magnet assembly coupled to at least one of the drive shaft and the impeller; and a driving coil assembly surrounding the driven magnet assembly and configured to drive the driven magnet assembly.

In Example 2, the magnetic drive system of Example 1 the driven magnet assembly is coupled to the drive shaft proximal the impeller.

In Example 3, the magnetic drive system of either of Example 1 or 2, the driving coil assembly includes a coil housing and a plurality of coil windings disposed within the coil housing.

In Example 4, the magnetic drive system of Example 3, the coil housing is disposed within a pump housing and surrounds the driven magnet assembly.

In Example 5, the magnetic drive system of any of Examples 1-4, the driven magnet assembly includes a permanent magnet disposed within a magnet cover.

In Example 6, a blood pump includes a pump housing; an impeller disposed within the pump housing; a drive shaft disposed within the pump housing, coupled to the impeller and configured to rotate with the impeller; a driven magnet assembly disposed within the pump housing and coupled to at least one of the drive shaft and the impeller; and a driving coil assembly disposed within the pump housing and surrounding the driven magnet assembly, and configured to drive the driven magnet assembly.

In Example 7, the blood pump of Example 6, the driven magnet assembly is coupled to the drive shaft proximal the impeller.

In Example 8, the blood pump of either of Example 6 or 7, the driving coil assembly includes a coil housing and a plurality of coil windings disposed within the coil housing, the coil housing is disposed within the pump housing and surrounds the driven magnet assembly.

In Example 9, the blood pump of any of Examples 6-8, the driven magnet assembly includes a permanent magnet disposed within a magnet cover.

In Example 10, the blood pump of any of Example 6-9, further includes a proximal bearing assembly, a proximal end of the drive shaft is rotatably retained by the proximal bearing assembly.

In Example 11, the blood pump of Example 10, the proximal bearing assembly includes a first bearing portion including a distal-facing bearing surface having a depression defined therein; and a second bearing portion including a proximal-facing bearing surface, the first and second bearing portions are configured to be coupled together to create a chamber configured to retain the proximal end of the drive shaft.

In Example 12, the blood pump of Example 10, the proximal bearing assembly includes a first bearing portion including a distal-facing bearing surface; a second bearing portion including a proximal-facing bearing surface; and a third bearing portion including a radially-facing bearing surface, the first, second, and third bearing portions are configured to be coupled together to create a chamber configured to retain the proximal end of the drive shaft.

In Example 13, the blood pump of either of Example 11 or 12, the first and second bearing portions are configured to be press-fit together, adhered together, or fastened together.

In Example 14, the blood pump of any of Examples 10-13, the first bearing portion having a first aperture defined therethrough, the second bearing portion having a second aperture defined therethrough, the first and second apertures are configured to be aligned when the first and second bearing portions are coupled such that an electrical conductor may be disposed through the first and second apertures, the electrical conductor electrically couples a power source to the driving coil assembly.

In Example 15, the blood pump of any of Examples 10-14, the distal end of the drive shaft is not retained by a distal bearing assembly.

In Example 16, a magnetic drive system of a blood pump, the magnetic drive system includes a drive shaft coupled to an impeller and configured to rotate with the impeller; a driven magnet assembly coupled to at least one of the drive shaft and the impeller; and a driving coil assembly electrically coupled to a power source, surrounding the driven magnet assembly, and configured to drive the driven magnet assembly.

In Example 17, the magnetic drive system of Example 16, the driven magnet assembly is coupled to the drive shaft proximal the impeller.

In Example 18, the magnetic drive system of Example 16, the driving coil assembly including a coil housing and a plurality of coil windings disposed within the coil housing.

In Example 19, the magnetic drive system of Example 18, the coil housing is disposed within a pump housing and surrounds the driven magnet assembly.

In Example 20, the magnetic drive system of Example 16, the driven magnet assembly comprises a permanent magnet disposed within a magnet cover.

In Example 21, a blood pump, includes a pump housing; an impeller disposed within the pump housing; a drive shaft disposed within the pump housing, coupled to the impeller and configured to rotate with the impeller; a driven magnet assembly disposed within the pump housing and coupled to at least one of the drive shaft and the impeller; and a driving coil assembly disposed within the pump housing, electrically coupled to a power source, surrounding the driven magnet assembly, and configured to drive the driven magnet assembly.

In Example 22, the blood pump of Example 21, the driven magnet assembly is coupled to the drive shaft proximal the impeller.

In Example 23, the blood pump of Example 21, the driving coil assembly includes a coil housing and a plurality of coil windings disposed within the coil housing, the coil housing is disposed within the pump housing and surrounds the driven magnet assembly.

In Example 24, the blood pump of Example 21, the driven magnet assembly includes a permanent magnet disposed within a magnet cover.

In Example 25, the blood pump of Example 21, further includes a proximal bearing assembly, a proximal end of the drive shaft is rotatably retained by the proximal bearing assembly.

In Example 26, the blood pump of Example 25, the proximal bearing assembly includes a first bearing portion including a distal-facing bearing surface having a depression defined therein; and a second bearing portion including a proximal-facing bearing surface, the first and second bearing portions are configured to be coupled together to create a chamber configured to retain the proximal end of the drive shaft.

In Example 27, the blood pump of Example 25, the proximal bearing assembly includes a first bearing portion including a distal-facing bearing surface; a second bearing portion including a proximal-facing bearing surface; and a third bearing portion including a radially-facing bearing surface, the first, second, and third bearing portions are configured to be coupled together to create a chamber configured to retain the proximal end of the drive shaft.

In Example 28, the blood pump of Example 27, the first and second bearing portions are configured to be press-fit together, adhered together, or fastened together.

In Example 29, the blood pump of Example 27, the first bearing portion having a first aperture defined therethrough, the second bearing portion having a second aperture defined therethrough, the first and second apertures are configured to be aligned when the first and second bearing portions are coupled such that an electrical conductor may be disposed through the first and second apertures, the electrical conductor electrically couples a power source to the driving coil assembly.

In Example 30, the blood pump of Example 25, the distal end of the drive shaft is not retained by a distal bearing assembly.

In Example 31, a blood pump, includes a pump housing; an impeller disposed within the pump housing; a drive shaft disposed within the pump housing, coupled to the impeller and configured to rotate with the impeller; a driven magnet assembly disposed within the pump housing and coupled to at least one of the drive shaft and the impeller; a driving coil assembly disposed within the pump housing, electrically coupled to a motor, surrounding the driven magnet assembly, and configured to drive the driven magnet assembly; and a proximal bearing assembly, a proximal end of the drive shaft is rotatably retained by the proximal bearing assembly, the proximal bearing assembly includes a first bearing portion including a distal-facing bearing surface; and a second bearing portion including a proximal-facing bearing surface, the first and second bearing portions are configured to be coupled together to create a chamber configured to retain the proximal end of the drive shaft.

In Example 32, the blood pump of Example 31, the driven magnet assembly is coupled to the drive shaft proximal the impeller.

In Example 33, the blood pump of Example 31, the driving coil assembly includes a coil housing and a plurality of coil windings disposed within the coil housing.

In Example 34, the blood pump of Example 33, the coil housing is disposed within the pump housing and surrounds the driven magnet assembly.

In Example 35, the blood pump of Example 34, the driven magnet assembly comprises a permanent magnet disposed within a magnet cover.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
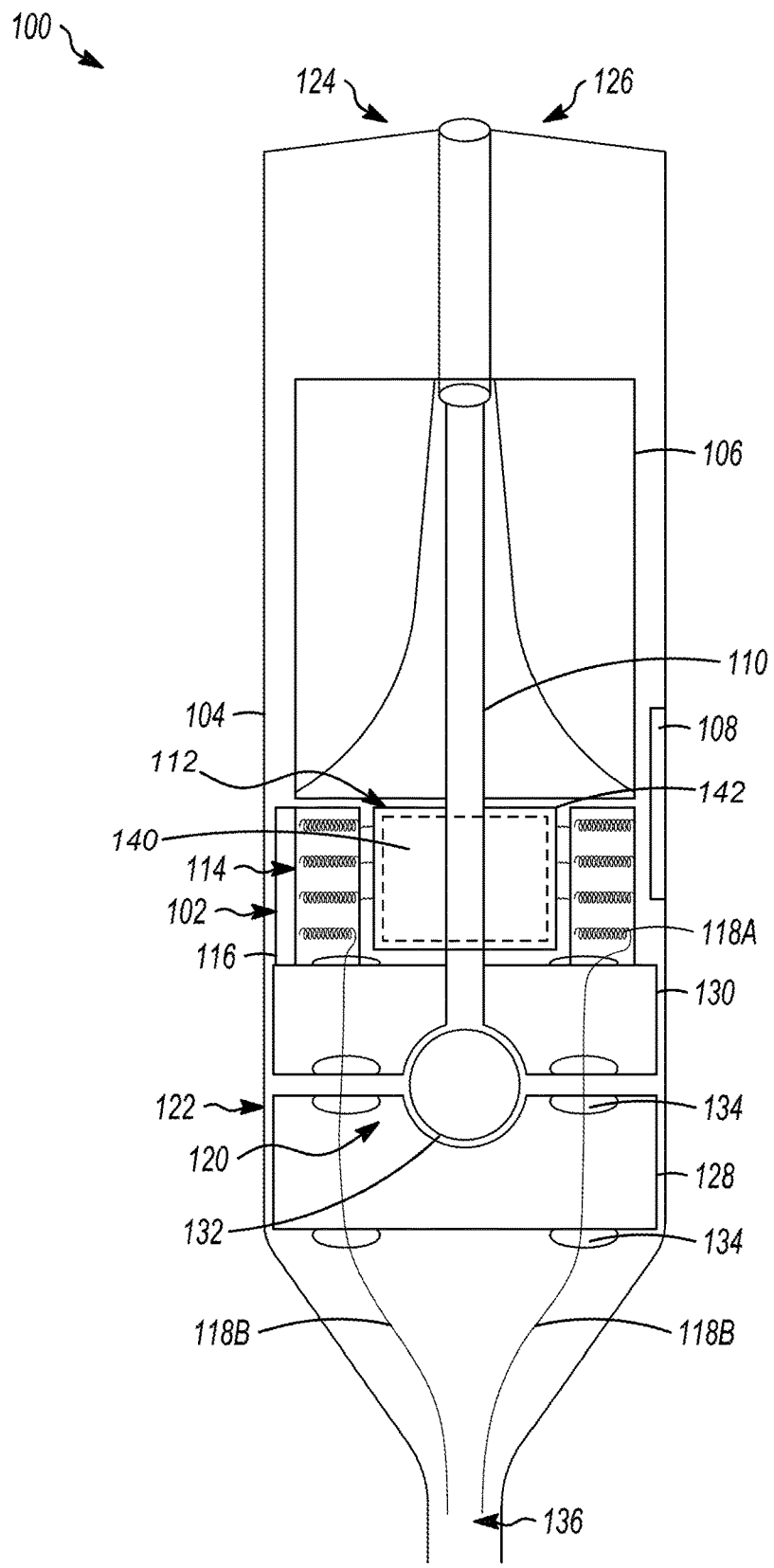
FIG. 1 depicts a cross-sectional side view of a portion of an illustrative percutaneous mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

Embodiments of the subject matter disclosed herein include blood pump and bearing designs that may facilitate reduction of the size of the form factor of mechanical circulatory assist devices by providing a compact electromagnetic driving system. In embodiments, metallic coils are implanted into a sealed housing. An electronic controller alternates the current of the coils to alter the polarity of the electromagnetic field to drive a permanent magnet coupled to an impeller. The permanent magnet is a strong magnet that may be encapsulated in a housing of some sort to eliminate risk of corrosion of the magnet or the need to coat the magnet. The rotary motion of the magnet drives impeller rotation to provide forward flow of blood and supply arterial blood pressure to ensure organs are perfused sufficiently in patients. The permanent magnet is bonded to a drive shaft. The drive shaft is placed in a bearing fitting in which the proximal end of the shaft is retained within a cavity defined in the proximal bearing assembly. This enables the shaft to rotate at speeds required to pump blood while maintaining the shaft and impeller concentric within the housing to maintain a consistent blade to tip gap. The fitting of the bearings is tightly controlled to an ID/OD tolerance between shaft and bearing such that the degrees of freedom are minimized to get a good bearing fit and keep blood out of the bearings, reducing the risk of hemolysis and thrombosis.

The forward flow of the blood over the coil housing acts as a means to dissipate heat from the electromagnetic coils. Given that air is a poor conductor of heat and can lead to heat buildup in the coil housing, which may limit motor performance if not addressed, steps may be taken to reduce the thermal resistance from the electromagnetic coil to the exterior of the housing by minimizing the amount of air in the coil housing. For example, the assembly of the coil within the housing may also be optimized for heat transfer by tolerancing assembly features to minimize the introduction of air gaps between components. The coil may also be coated through atomic layer deposition of a ceramic to enable a tight assembly within the housing that minimizes gap between assembled components to optimize heat transfer without creating the risk of an electrical short circuit. In addition, the coil housing may have a non-electrolytic, high thermal conductivity liquid to increase heat transfer from the electromagnetic coil to the exterior of the coil housing. The optimization of heat transfer to drive heat away from the electromagnet coils can increase the torque output for an equivalent form factor device, or reduce the size of coil required, which may facilitate easier deliverability of the device and optimal positioning. Also, by eliminating a separate motor housing and motor in favor of a coil that in turn drives the magnet of the impeller, the length required to house such components may be greatly reduced from existing devices.

FIG. 1 depicts a cross-sectional side view of a portion of an illustrative percutaneous mechanical circulatory support device 100 (also referred to herein, interchangeably, as a "blood pump"), in accordance with embodiments of the subject matter disclosed herein. As shown in FIG. 1, the circulatory support device 100 includes a magnetic drive system 102 disposed within a pump housing 104. The magnetic drive system 102 is configured to drive an impeller 106 to provide a flow of blood through the device 100. The impeller 106 is disposed within the pump housing 104, which includes a number of outlet apertures 108 defined therein.

As shown in FIG. 1, the magnetic drive system 102 includes a drive shaft 110 coupled to the impeller 106 and configured to rotate with the impeller 106. As shown, the drive shaft 110 is at least partially disposed within the impeller 106. In embodiments, the drive shaft 110 may be made of any number of different rigid materials such as, for example, steel, titanium alloys, cobalt chromium alloys, nitinol, high-strength ceramics, and/or the like. A driven magnet assembly 112 is coupled to at least one of the drive shaft 110 and the impeller 106. In embodiments, for example, the driven magnet assembly 112 may be coupled to the drive shaft 110 proximal the impeller 106. In other embodiments, the driven magnet assembly 112 may be coupled directly to the impeller 106, while, in some embodiments, the driven magnet assembly 112 may be coupled to the drive shaft 110 and the impeller 106. The magnetic drive system 102 includes a driving coil assembly 114 electrically coupled to a power source (not shown). The magnetic driving coil assembly 114 surrounds the driven magnet assembly 112 and is configured to drive the driven magnet assembly 112.

The driving coil assembly 114 includes a coil housing 116 and a number of coil windings 118A disposed within the coil housing 116. The electromagnetic field could be generated from copper, graphene, or other high thermal conductivity materials in coiled configurations. The driving coil assembly 114 may include any number of coil windings 118A arranged in any number of configurations within the coil housing 116. In embodiments, the coil housing 116 may actually include multiple, separate housings. The coil housing 116 is disposed within the pump housing 104 and may circumferentially or longitudinally surround the driven magnet assembly 112. As shown, in embodiments, the driven magnet assembly 112 may include a permanent magnet 140 disposed within a magnet cover 142, which may be hermetically sealed.

A controller (not shown) is operably coupled, via electrical conductors 1188 to the driving coil assembly 114 and is configured to control the driving coil assembly 114. The controller may be disposed within the pump housing 104 in embodiments, or, in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

Figure 3:
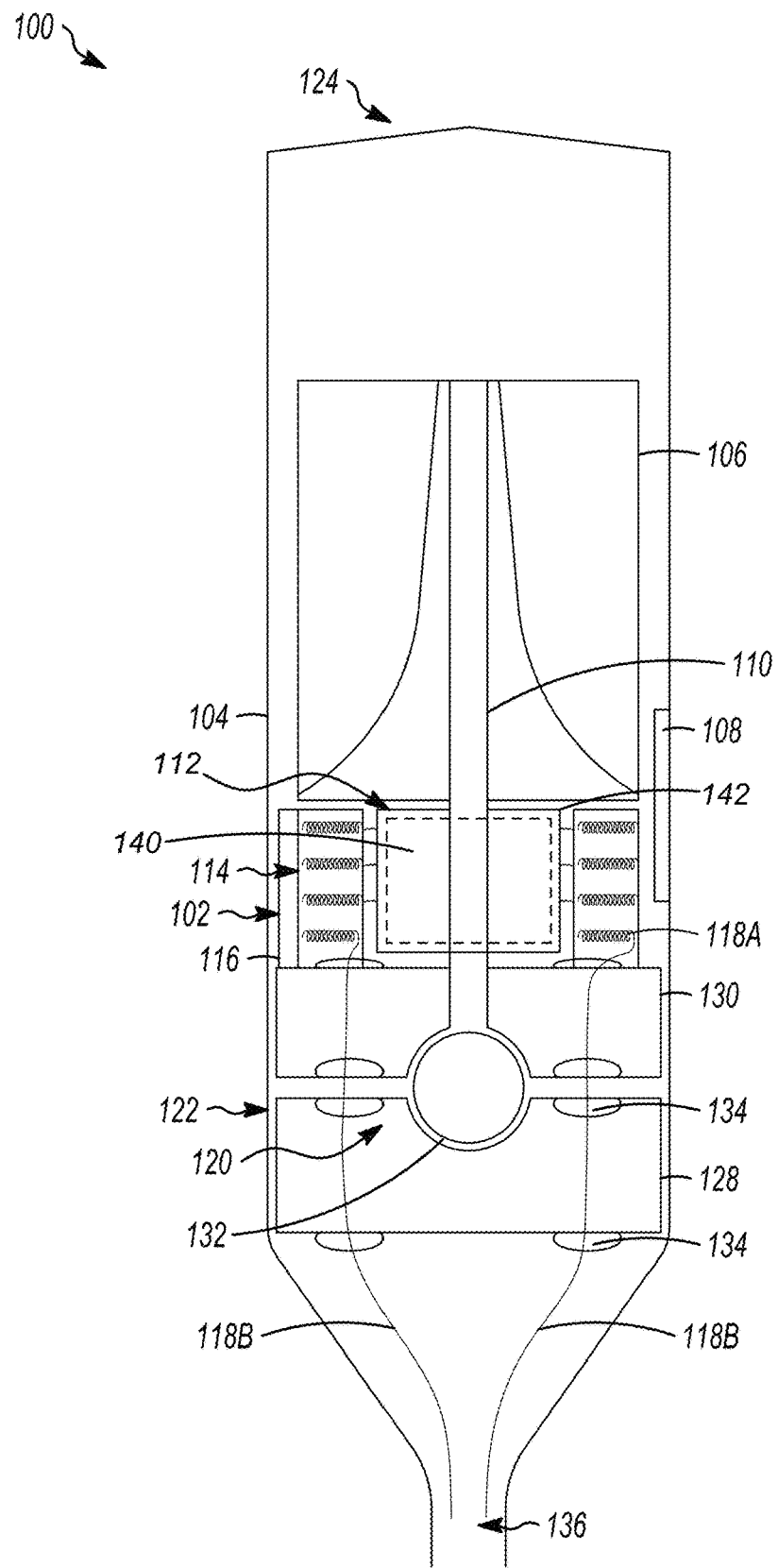
FIG. 3 depicts a cross-sectional side view of a portion of another illustrative percutaneous mechanical circulatory support device, in accordance with embodiments of the subject matter disclosed herein.

As shown, the impeller 106 is maintained in its orientation by the drive shaft 110, which is retained at a proximal end 120 by a proximal bearing assembly 122 and at a distal end 124 by a distal bearing assembly 126. According to embodiments, the proximal bearing assembly 122 and the distal bearing assembly 126 may include different types of bearings. According to embodiments, the proximal bearing assembly 122 and/or the distal bearing assembly 126 may include lubrication, while in other embodiments, one and/or the other may not include lubrication. In embodiments and as shown in FIG. 3, the drive shaft 110 may be held rigidly enough by the proximal bearing assembly 122 that a distal bearing assembly is not needed, in which case the drive shaft 110 is not held in place by a distal bearing assembly.

As shown in FIG. 1, the proximal bearing assembly 122 may include a first bearing portion 128 and a second bearing portion 130, configured to be coupled together to form a chamber 132 that is configured to retain the proximal end 120 of the drive shaft 110. According to embodiments, the first and second bearing portions 128 and 130 may be configured to be press-fit together, coupled using interlocking grooves, coupled using an adhesive, coupled using pins, coupled using fasteners, and/or the like. In embodiments, apertures 134 are defined through the proximal bearing assembly 122. The conductors 1188 pass through the apertures 134 to electrically connect the coil windings 118A with the power source. The proximal bearing assembly 122 may be configured to seal the catheter 136 from the blood.

The illustrative circulatory support device 100 shown in FIG. 1 is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2A:
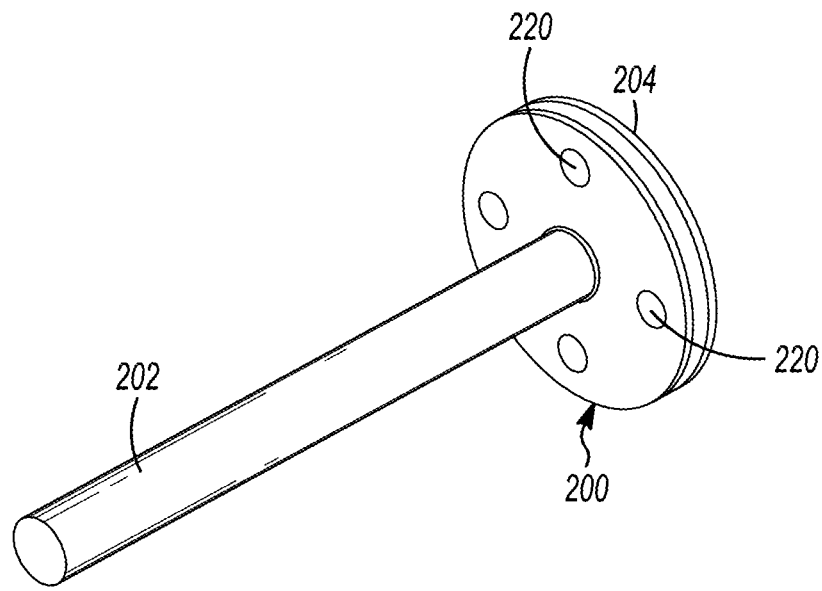
FIG. 2A is a perspective view of a proximal bearing assembly retaining a drive shaft, in accordance with embodiments of the subject matter disclosed herein.
Figure 2B:
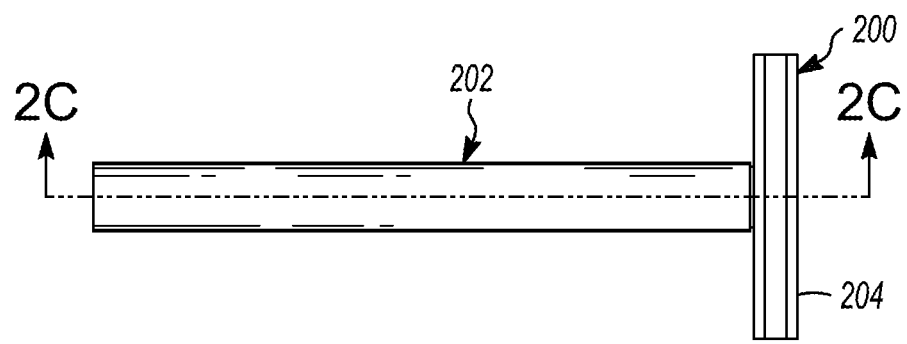
FIG. 2B is a side view of the proximal bearing assembly and drive shaft of FIG. 2A, in accordance with embodiments of the subject matter disclosed herein.
Figure 2C:
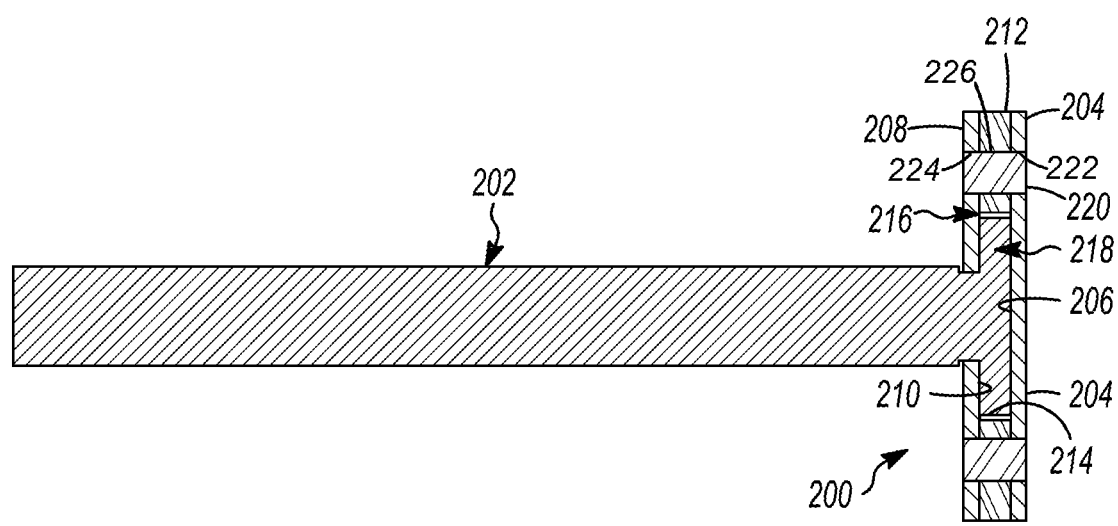
FIG. 2C is a cross-sectional side view, taken along the line A-A, of the proximal bearing assembly and drive shaft depicted in FIGS. 2A and 2B, in accordance with embodiments of the subject matter disclosed herein.

As described above, with regard to FIG. 1, embodiments of the blood pump include a proximal bearing assembly configured to maintain the drive shaft in position and to seal the catheter from the blood, while allowing electrical conductors to pass through to the coil windings. In embodiments, a proximal bearing assembly may include three or more bearing portions. For example, FIG. 2A is a perspective view of a proximal bearing assembly 200 retaining a drive shaft 202, in accordance with embodiments of the subject matter disclosed herein; FIG. 2B is a side view of the proximal bearing assembly 200 and drive shaft 202 of FIG. 2A, in accordance with embodiments of the subject matter disclosed herein; and FIG. 2C is a cross-sectional side view, taken along the line A-A, of the proximal bearing assembly 200 and drive shaft 202 depicted in FIGS. 2A and 2B, in accordance with embodiments of the subject matter disclosed herein. According to embodiments, the circulatory support device, and/or any number of various components thereof, may be the same as, or similar to, corresponding components of the circulatory support device 100 depicted in FIG. 1.

As shown in FIGS. 2A-2C, the proximal bearing assembly 200 may include a first bearing portion 204 comprising a distal-facing bearing surface 206, a second bearing portion 208 comprising a proximal-facing bearing surface 210, and a third bearing portion 212 having a radially-facing bearing surface 214. As shown, the first, second, and third bearing portions 204, 208, and 212 are configured to be coupled together, with the third bearing portion 212 disposed between the first and the second bearing portions 204 and 208. When coupled together, the bearing portions 204, 208, and 212 form a cavity 216 configured to retain a proximal end 218 of the drive shaft 202. As shown, for example, the proximal end 218 of the drive shaft 202 may be formed as a disc, configured to fit in the cavity 216 within the bearing assembly 200. In embodiments, such as shown in FIG. 1, the proximal end 218 of the drive shaft 202 may include a ball or other at least partially rounded shape, configured to be retained within the cavity 216. The head of the drive shaft 202 may contain internal grooves to create pressure as the head rotates, reducing friction and torque required to operate the pump.

The bearing portions 204, 208, and 212 may be coupled together using any number of different coupling techniques and/or mechanisms. For example, in embodiments, the bearing portions 204, 208, and 212 may be press-fit and secured with one or more pins 220, as shown in FIGS. 2A-2C. In embodiments, the bearing portions 204, 208, and 212 may be adhered together using an adhesive, fastened together using one or more fasteners, and/or the like. The proximal bearing assembly may be attached to the impeller housing via laser welding, solder reflow, or adhesive application, and/or the like.

Further, in embodiments, apertures may be provided through the proximal bearing assembly 200 to facilitate connecting the coil windings with the power source. For example, the first bearing portion 204 may include a first aperture 222 defined therethrough, the second bearing portion 208 may include a second aperture 224 defined therethrough, and the third bearing portion 212 may include a third aperture 226 defined therethrough, such that the first, second, and third apertures 222, 224, and 226 are configured to be aligned when the first and second bearing portions 204 and 208 are coupled such that an electrical conductor may be disposed through the apertures 222, 224, and 226, wherein the electrical conductor electrically couples a power source to the driving coil assembly. In embodiments, the proximal bearing assembly may include only two bearing portions, in which case, each bearing portion may include one or more apertures corresponding to one or more apertures in the other bearing portion.

The illustrative proximal bearing assembly 200 and drive shaft 202 shown in FIGS. 2A-2C are not intended to suggest any limitation as to the scope of use or functionality of embodiments of the present disclosure. The illustrative proximal bearing assembly 200 and drive shaft 202 also should not be interpreted as having any dependency or requirement related to any single component or combination of components illustrated therein. Additionally, various components depicted in FIGS. 2A-2C may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A magnetic drive system of a blood pump, the magnetic drive system comprising:
    a drive shaft coupled to an impeller and configured to rotate with the impeller;
    a driven magnet assembly coupled to at least one of the drive shaft and the impeller;
    a driving coil assembly electrically coupled to a power source, surrounding the driven magnet assembly, and configured to drive the driven magnet assembly, the driving coil assembly surrounding the driven magnet and not surrounding the impeller;
    a proximal bearing assembly comprising:
        a first bearing portion disposed proximally relative to the driven magnet assembly; and
        a second bearing portion disposed distally relative to the first bearing portion and proximally relative to the driven magnet assembly.

2. The magnetic drive system of claim 1, wherein the driven magnet assembly is coupled to the drive shaft proximal the impeller.

3. The magnetic drive system of claim 1, the driving coil assembly comprising a coil housing and a plurality of coil windings disposed within the coil housing.

4. The magnetic drive system of claim 3, wherein the coil housing is disposed within a pump housing and surrounds the driven magnet assembly.

5. The magnetic drive system of claim 1, wherein the driven magnet assembly comprises a permanent magnet disposed within a magnet cover.

6. A blood pump, comprising:
a pump housing;
an impeller disposed within the pump housing;
a drive shaft disposed within the pump housing, coupled to the impeller and configured to rotate with the impeller;
a driven magnet assembly disposed within the pump housing and coupled to at least one of the drive shaft and the impeller;
a driving coil assembly disposed within the pump housing, electrically coupled to a power source, surrounding the driven magnet assembly and not surrounding the impeller, and configured to drive the driven magnet assembly;
a proximal bearing assembly, wherein a proximal end of the drive shaft is rotatably retained by the proximal bearing assembly; the proximal bearing assembly comprising:
a first bearing portion comprising a distal-facing bearing surface;
a second bearing portion comprising a proximal-facing bearing surface; and
a third bearing portion comprising a radially-facing bearing surface, wherein the first, second, and third bearing portions are configured to be coupled together to create a chamber configured to retain the proximal end of the drive shaft.

7. The blood pump of claim 6, wherein the driven magnet assembly is coupled to the drive shaft proximal to the impeller.

8. The blood pump of claim 6, the driving coil assembly comprising a coil housing and a plurality of coil windings disposed within the coil housing, wherein the coil housing is disposed within the pump housing and surrounds the driven magnet assembly.

9. The blood pump of claim 6, wherein the driven magnet assembly comprises a permanent magnet disposed within a magnet cover.

10. The blood pump of claim 6, wherein the first and second bearing portions are configured to be press-fit together, adhered together, or fastened together.

11. The blood pump of claim 6, the first bearing portion having a first aperture defined therethrough, the second bearing portion having a second aperture defined therethrough, wherein the first and second apertures are configured to be aligned when the first and second bearing portions are coupled such that an electrical conductor may be disposed through the first and second apertures, wherein the electrical conductor electrically couples a power source to the driving coil assembly.

12. The blood pump of claim 6, wherein a distal end of the drive shaft is not retained by a distal bearing assembly.

13. A blood pump, comprising:
a pump housing;
an impeller disposed within the pump housing;
a drive shaft disposed within the pump housing, coupled to the impeller and configured to rotate with the impeller;
a driven magnet assembly disposed within the pump housing and coupled to at least one of the drive shaft and the impeller;
a driving coil assembly disposed within the pump housing, electrically coupled to a power source, surrounding the driven magnet assembly, and configured to drive the driven magnet assembly; and
a proximal bearing assembly, wherein a proximal end of the drive shaft is rotatably retained by the proximal bearing assembly, the proximal bearing assembly comprising:
a first bearing portion comprising a distal-facing bearing surface and a first aperture defined therethrough; and
a second bearing portion comprising a proximal-facing bearing surface and a second aperture defined therethrough, wherein the first and second bearing portions are configured to be coupled together to create a chamber configured to retain the proximal end of the drive shaft; and
wherein the first and second apertures are configured to be aligned when the first and second bearing portions are coupled such that an electrical conductor may be disposed through the first and second apertures, wherein the electrical conductor electrically couples the power source to the driving coil assembly.

14. The blood pump of claim 13, wherein the driven magnet assembly is coupled to the drive shaft proximal to the impeller.

15. The blood pump of claim 13, the driving coil assembly comprising a coil housing and a plurality of coil windings disposed within the coil housing.

16. The blood pump of claim 15, wherein the coil housing is disposed within the pump housing and surrounds the driven magnet assembly.

17. The blood pump of claim 16, wherein the driven magnet assembly comprises a permanent magnet disposed within a magnet cover.

18. The magnetic drive system of claim 1, wherein the first bearing portion and the second bearing portion are configured to be coupled together to create a chamber configured to retain a proximal end of the drive shaft.

* * * * *